United States Patent
Gottipati et al.

(10) Patent No.: US 11,504,335 B2
(45) Date of Patent: Nov. 22, 2022

(54) INCREASED CELL RETENTION IN DISEASED SITE WHEN CELLS ENCAPSULATED IN GELATIN METHACRYLATE AND POLYETHYLENE GLYCOL DIACRYLATE HYDROGELS

(71) Applicant: University of Kentucky Research Foundation, Lexington, KY (US)

(72) Inventors: Anuhya Gottipati, Lexington, KY (US); Irina Kalashnikova, Lexington, KY (US); Ahmed Abdel-Latif, Lexington, KY (US); Bradley J. Berron, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 169 days.

(21) Appl. No.: 16/445,046

(22) Filed: Jun. 18, 2019

(65) Prior Publication Data
US 2019/0380970 A1 Dec. 19, 2019

Related U.S. Application Data

(60) Provisional application No. 62/689,498, filed on Jun. 25, 2018, provisional application No. 62/686,392, filed on Jun. 18, 2018.

(51) Int. Cl.
*A61K 9/48* (2006.01)
*A61K 9/00* (2006.01)
*A61P 9/10* (2006.01)
*A61K 35/44* (2015.01)
*A61K 35/28* (2015.01)

(52) U.S. Cl.
CPC .......... *A61K 9/4825* (2013.01); *A61K 9/0019* (2013.01); *A61K 35/28* (2013.01); *A61K 35/44* (2013.01); *A61P 9/10* (2018.01)

(58) Field of Classification Search
CPC .................................................. A61K 9/4825
See application file for complete search history.

(56) References Cited

U.S. PATENT DOCUMENTS

| | | | |
|---|---|---|---|
| 8,088,370 B2 | 1/2012 | Pecora et al. | |
| 8,202,701 B2 | 6/2012 | Boyan et al. | |
| 8,293,510 B2 | 10/2012 | Detamore et al. | |
| 8,361,781 B2 | 1/2013 | Morgan et al. | |
| 8,414,879 B2 | 4/2013 | Gemeinhart | |
| 8,728,747 B2 | 5/2014 | Haval | |
| 8,993,538 B2 | 3/2015 | Cohen et al. | |
| 9,393,267 B2 | 7/2016 | Han | |
| 9,428,565 B2 | 8/2016 | Shah | |
| 9,587,221 B2 | 3/2017 | Lipke et al. | |
| 2008/0193536 A1 | 8/2008 | Khademhosseini et al. | |
| 2012/0114618 A1 | 5/2012 | Nolta | |
| 2017/0112971 A1 | 4/2017 | Spiller | |
| 2017/0196818 A1 | 7/2017 | Jae-Won et al. | |

FOREIGN PATENT DOCUMENTS

| | | | | |
|---|---|---|---|---|
| WO | WO2016154070 A1 | * | 9/2016 | ............. B29C 67/00 |
| WO | WO 2017/151773 | | 9/2017 | |
| WO | WO2019198086 A1 | * | 10/2019 | ............... A61F 9/00 |

OTHER PUBLICATIONS

Gabriela Romero, Protective Polymer Coatings for High-Throughput, High-Purity Cellular Isolation, ACS Appl. Mater. Interfaces 2015, 7, 17598-17602 (Year: 2015).*

Jacob L. Lilly, Comparison of eosin and fluorescein conjugates for the photoinitiation of cellcompatible polymer coatings, PLoS ONE 13 (1): e0190880, publication date Jan. 8, 2018 (Year: 2018).*

Wei Zhu, 3D bioprinting mesenchymal stem cell-laden construct with core-shell nanospheres for cartilage tissue engineering, Nanotechnology 29 (2018) 185101 (10pp), publication date: Mar. 8, 2018 (Year: 2018).*

Yufei Ma et al, Bioprinting-based PDLSC-ECM Screening for in vivo Repair of Alveolar Bone Defect using Cell-laden, Injectable and Photocrosslinkable Hydrogels, ACS Biomater. Sci. Eng., Publication Date: Oct. 13, 2017 (Year: 2017).*

Wei Zhu et al, 3D printing scaffold coupled with low level light therapy for neural tissue regeneration, Biofabrication 9, 2017 (Year: 2017).*

Peter, et al., Manipulation of blended hydrogel matrix for 3D cell culture, Event Abstract, 2017; pp. 1-2.

Yu, et al., Fabrication of gelatin- and collagen-based hydrogels for controlled drug release, Frontiers, 2026; pp. 1-2.

Li, et al., Microfabrication of Cell-Laden Hydrogels for Engineering Mineralized and Load Bearing Tissues, 2015. pp. 15-22.

Hastings, et al., Drug and cell delivery for cardiac regeneration, Advanced Drug Delivery Reviews 84 (2015) 85-106.

Kim, et al., Fabrication of poly(ethylene glycol): gelatin methacrylate composite nanostructures with tunable stiffness and degradation for vascular tissue engineering, Biofabrication 6 (2014) 024112 (12pp).

Hutson, et al., Synthesis and Characterization of Tunable Poly(Ethylene Glycol): Gelatin Methacrylate Composite Hydrogels, Tissue Engineering: Part A, vol. 17, Nos. 13 and 14, 2011, pp. 1713-1723.

Nichol, et al., Cell-laden microengineered gelatin methacrylate hydrogels, Biomaterials 31 (2010) 5536-5544.

Lu, et al., Functional Improvement of Infarcted Heart by Co-Injection of Embryonic Stem Cells with Temperature-Responsive Chitosan Hydrogel, Tissue Engineering: Part A, vol. 15, No. 6, 2009, pp. 1437-1447.

Avens, et al., Polymerization Behavior and Polymer Properties of Eosin-Mediated Surface Modification Reactions, Polymer (Guildf). Oct. 17, 2008; 49(22): 4762-4768.

(Continued)

*Primary Examiner* — Mark V Stevens
*Assistant Examiner* — Alparslan Asan
(74) *Attorney, Agent, or Firm* — Stites & Harbison PLLC; Mandy Wilson Decker

(57) ABSTRACT

The presently-disclosed subject matter relates to compositions of dual layer encapsulated cells, dual layer encapsulated stem cells. The presently-disclosed subject matter further relates to methods for improving retention of cells in vivo at a site of injury.

15 Claims, 11 Drawing Sheets

(56) References Cited

OTHER PUBLICATIONS

Abbott, J.D., et al., Stromal cell-derived factor-1alpha plays a critical role in stem cell recruitment to the heart after myocardial infarction but is not sufficient to induce homing in the absence of injury. Circulation, 2004. 110(21): p. 3300-5.

Afzal, M.R., et al., Adult Bone Marrow Cell Therapy for Ischemic Heart Disease: Evidence and Insights From Randomized Controlled Trials. Circ Res, 2015. 117(6): p. 558-75.

Agarwal, U., et al., Role of cardiac myocyte CXCR4 expression in development and left ventricular remodeling after acute myocardial infarction. Circ Res, 2010. 107(5): p. 667-76.

Arnaoutova, I., et al., Basement membrane matrix (BME) has multiple uses with stem cells. Stem Cell Rev, 2012. 8(1): p. 163-9.

Asahara, T., A. Kawamoto, and H. Masuda, Concise Review: Circulating Endothelial Progenitor Cells for Vascular Medicine. Stem Cells, 2011. 29(11): p. 1650-1655.

Blackburn, N.J., et al., Timing underpins the benefits associated with injectable collagen biomaterial therapy for the treatment of myocardial infarction. Biomaterials, 2015. 39: p. 182-92.

Brenner, W., et al., 111In-labeled CD34+ hematopoietic progenitor cells in a rat myocardial infarction model. J Nucl Med, 2004. 45(3): p. 512-8.

D'Souza, S., et al., Engineering of cell membranes with a bisphosphonate-containing polymer using ATRP synthesis for bone targeting. Biomaterials, 2014. 35(35): p. 9447-58.

Epelman, S., P.P. Liu, and D.L. Mann, Role of innate and adaptive immune mechanisms in cardiac injury and repair. Nat Rev Immunol, 2015. 15(2): p. 117-29.

Fedorovich, N.E., et al., Hydrogels as extracellular matrices for skeletal tissue engineering: state-of-the-art and novel application in organ printing. Tissue Eng, 2007. 13(8): p. 1905-25.

Gao, E., et al., A novel and efficient model of coronary artery ligation and myocardial infarction in the mouse. Circ Res, 2010. 107(12): p. 1445-53.

Hamidi, M., A. Azadi, and P. Rafiei, Hydrogel nanoparticles in drug delivery. Adv Drug Deliv Rev, 2008. 60(15): p. 1638-49.

Hofmann, M., et al., Monitoring of bone marrow cell homing into the infarcted human myocardium. Circulation, 2005. 111(17): p. 2198-202.

Holladay, C.A., et al., Recovery of cardiac function mediated by MSC and interleukin-10 plasmid functionalised scaffold. Biomaterials, 2012. 33(5): p. 1303-14.

Kavanagh, D.P., J. Robinson, and N. Kalia, Mesenchymal stem cell priming: fine-tuning adhesion and function. Stem Dell Rev, 2014. 10(4): p. 587-99.

Kiessling, A. and P. Henriksson, Time trends of chest pain symptoms and health related quality of life in coronary artery disease. Health and quality of life outcomes, 2007. 5(1): p. 13.

Klyachkin, Y.M., et al., Pharmacological Elevation of Circulating Bioactive Phosphosphingolipids Enhances Myocardial Recovery After Acute Infarction. Stem Cells Transl Med, 2015.

Kucia, M., et al., CXCR4-SDF-1 signalling, locomotion, chemotaxis and adhesion. J Mol Histol, 2004. 35(3): p. 233-45.

Lilly, J.L. and B.J. Berron, The Role of Surface Receptor Density in Surface-Initiated Polymerizations for Cancer Cell Isolation. Langmuir, 2016. 32(22): p. 5681-9.

Lilly, J.L., et al., Characterization of molecular transport in ultrathin hydrogel coatings for cellular immunoprotection. Biomacromolecules, 2015. 16(2): p. 541-9.

Lilly, J.L., et al., Interfacial polymerization for colorimetric labeling of protein expression in cells. PLoS One, 2014. 9(12): p. e115630.

Lin, C.C. and K.S. Anseth, PEG hydrogels for the controlled release of biomolecules in regenerative medicine. Pharm Res, 2009. 26(3): p. 631-43.

Liu, G., et al., A VEGF delivery system targeting MI improves angiogenesis and cardiac function based on the tropism of MSCs and layer-by-layer self-assembly. Biomaterials, 2017. 127: p. 117-131.

Losordo, D.W., et al., Intramyocardial, autologous CD34+ cell therapy for refractory angina. Circ Res, 2011. 109(4): p. 428-36.

MacArthur, J.W., Jr., et al., Sustained release of engineered stromal cell-derived factor 1-alpha from injectable hydrogels effectively recruits endothelial progenitor cells and preserves ventricular function after myocardial infarction. Circulation, 2013. 128(11 Suppl 1): p. S79-86.

Marquez-Curtis, L.A., et al., The ins and outs of hematopoietic stem cells: studies to improve transplantation outcomes. Stem cell reviews, 2011. 7(3): p. 590-607.

McQuibban, G.A., et al., Matrix metalloproteinase activity inactivates the CXC chemokine stromal cell-derived factor-1. J Biol Chem, 2001. 276(47): p. 43503-8.

McQuibban, G.A., et al., Matrix metalloproteinase processing of monocyte chemoattractant proteins generates CC chemokine receptor antagonists with anti-inflammatory properties in vivo. Blood, 2002. 100(4): p. 1160-7.

Moran, A.E., et al., Temporal Trends in Ischemic Heart Disease Mortality in 21 World Regions, 1980-2010: The Global Burden of Disease 2010 Study. Circulation, 2014.

Nahrendorf, M., et al., The healing myocardium sequentially mobilizes two monocyte subsets with divergent and complementary functions. J Exp Med, 2007. 204(12): p. 3037-47.

Nash, M.E., et al., Thermoresponsive substrates used for the expansion of human mesenchymal stem cells and the preservation of immunophenotype. Stem Cell Rev, 2013. 9(2): p. 148-57.

Peterson, J.T., et al., Evolution of matrix metalloprotease and tissue inhibitor expression during heart failure progression in the infarcted rat. Cardiovasc Res, 2000. 46(2): p. 307-15.

Purcell, B.P., et al., Synergistic effects of SDF-1alpha chemokine and hyaluronic acid release from degradable hydrogels on directing bone marrow derived cell homing to the myocardium. Biomaterials, 2012. 33(31): p. 7849-57.

Quyyumi, A., et al., One year follow-up results from PRESERVE-AMI: a randomized, double-blind, placebo controlled clinical trial of intracoronary infusion of autologous CD34+ cells in patients with left ventricular dysfunction post STEMI. J Am Coll Cardiol, 2015. 55(10): p. A1593.

Quyyumi, A.A., et al., PreSERVE-AMI: A Randomized, Double-Blind, Placebo-Controlled Clinical Trial of Intracoronary Administration of Autologous CD34+ Cells in Patients With Left Ventricular Dysfunction Post STEMI. Circ Res, 2017. 120(2): p. 324-331.

Ratajczak, M.Z., et al., Pivotal role of paracrine effects in stem cell therapies in regenerative medicine: can we translate stem cell-secreted paracrine factors and microvesicles into better therapeutic strategies? Leukemia, 2012. 26(6): p. 1166-73.

Romero, G., et al., Protective Polymer Coatings for High-Throughput, High-Purity Cellular Isolation. ACS Appl Mater Interfaces, 2015. 7(32): p. 17598-602.

Sarig, U. and M. Machluf, Engineering cell platforms for myocardial regeneration. Expert Opin Biol Ther, 2011. 11(8): p. 1055-77.

Serpooshan, V., et al., The effect of bioengineered acellular collagen patch on cardiac remodeling and ventricular function post myocardial infarction. Biomaterials, 2013. 34(36): p. 9048-55.

van der Laan, A.M., et al., Monocyte subset accumulation in the human heart following acute myocardial infarction and the role of the spleen as monocyte reservoir. Eur Heart J, 2014. 35(6): p. 376-85.

Wojakowski, W., et al., Very small embryonic-like stem cells in cardiovascular repair. Pharmacol Ther, 2011. 129(1): p. 21-8.

Zhou, Y., et al., Effects of Human Fibroblast-Derived Extracellular Matrix on Mesenchymal Stem Cells. Stem Cell Rev, 2016. 12(5): p. 560-572.

Zuba-Surma, E.K., et al., Transplantation of expanded bone marrow-derived very small embryonic-like stem cells (VSEL-SCs) improves left ventricular function and remodelling after myocardial infarction. J Cell Mol Med, 2011. 15(6): p. 1319-28.

Zuba-Surma, E.K., et al., Very small embryonic-like stem cells: biology and therapeutic potential for heart repair. Antioxid Redox Signal, 2011. 15(7): p. 1821-34.

* cited by examiner

A

Picrosirius Red    Calcein    Merged

B

A

B

E

INCREASED CELL RETENTION IN DISEASED SITE WHEN CELLS ENCAPSULATED IN GELATIN METHACRYLATE AND POLYETHYLENE GLYCOL DIACRYLATE HYDROGELS

GOVERNMENT INTEREST

This invention was made with government support under grant numbers CBET-1351531 and R01 HL 127682 awarded by the National Science Foundation and National Institutes of Health, respectively. The government has certain rights in the invention.

RELATED APPLICATIONS

This application is related to U.S. Provisional Application Ser. Nos. 62/686,392 filed Jun. 18, 2018 and 62/689,498 filed Jun. 25, 2018, the entire disclosures of which are incorporated herein by this reference.

TECHNICAL FIELD

The present invention relates to a composition of encapsulated stem cells and a method for improving retention of a stem cell at an in vivo site of injury.

BACKGROUND

Ischemic heart disease, often caused by acute myocardial infarction (AMI), is the leading cause of morbidity and mortality in the developed world [1]. While modern cardiology has achieved significant strides in revascularization and medical management, a significant portion of AMI patients progress to develop ischemic cardiomyopathy (ICM) and heart failure (HF) [2]. Bone marrow derived stem cells (BMSCs) are an attractive therapeutic target for cardiac regeneration and have been extensively investigated in animal experiments and human translational studies. However, low cell engraftment after transplantation has limited the cardiac function recovery for BMSC therapy [3]. Indeed, only a small fraction of transplanted cells remain at the injury site 24 h after injection into the heart wall [4]. Recent clinical studies [5] and meta-analyses [6] indicate the benefit of BMSC therapy is directly correlated with the quantity of cells injected, where the injection of more cells provides greater functional recovery. Clinically, the number of harvested BMSCs is limited, and larger harvest procedures are hazardous given the high-risk population in question. Additionally, ex vivo expansion to expand stem cells for further clinical use carries the risk of infection of cell phenotype changes. Therefore, efforts directed towards enhanced cell retention after transplantation are desperately needed.

Biomaterial based cardiac tissue engineering has been widely used in animal and human studies [7-9]. These studies have addressed two major limitations of current cardiac regenerative therapies, namely cytokine release to enhance the therapeutic potential of stem cells and providing mechanical support (scaffolding) to the damaged muscle through biocompatible grafts. Strategies aimed at the local sustained delivery of recombinant SDF-1 (rSDF-1) through its integration in cross-linked hyaluronic acid (HA) hydrogels resulted in enhanced bone marrow cell engraftment in the heart [10]. Furthermore, the effect of HA impregnated with an engineered SDF-1 mimetic led to significant reduction in cardiac remodeling and fibrosis at 4 weeks after AMI [11]. Other studies have focused on the delivery of other cytokines such as VEGF in cell based coatings including encapsulated mesenchymal stem cells (MSCs) using collagen and alginate polyelectrolytes [12]. Additionally, the use of biocompatible scaffolds to mitigate post-AMI adverse cardiac remodeling has demonstrated safety and therapeutic success in animal and early pre-clinical studies. Scaffolding material are either natural or synthetic [13], and in early studies natural materials appear to be more biodegradable, biocompatible, and have an advantage in recreating the native cardiac microenvironment [14]. In a previous study, Russell et al showed an increased cell binding to bone fragments (in vitro), when the cell membranes were modified with a bisphosphonate-containing polymer [15]. While these strategies have achieved success in proof of concept studies, they do not address the poor retention of stem cells after transplantation.

In the present invention, an adhesive biocompatible coating was used on the exterior of BM cells (BMCs) to improve the retention of BMCs in the heart. These efforts build upon earlier successes in generating biosynthetic polymer coating on living cells. These coatings were designed using polyethylene glycol (PEG) based polymers to completely coat cells for purification purposes [16]. PEG based coatings allow essential nutrient transport thus preserving cell viability [17]. Gelatin based cell coatings are demonstrated that are safe, biodegradable, and enhances cell retention in the ischemic myocardium without significantly impairing cell metabolism or survival.

SUMMARY

The presently-disclosed subject matter meets some or all of the above-identified needs, as will become evident to those of ordinary skill in the art after a study of information provided in this document.

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned, likewise, those features can be applied to other embodiments of the presently disclosed subject matter, whether listed in this Summary or not. To avoid excessive repetition, this Summary does not list or suggest all possible combinations of such features.

In one embodiment of the present invention, the composition comprises a cell encapsulated in a dual layer comprising an inner layer comprising the cell and a photoinitiator, and an outer layer comprising a hydrogel and substantially surrounding the inner layer.

In a further embodiment of the present invention, the photoinitiator is anchored to the cell.

In another embodiment of the present invention, the composition comprises a stem cell encapsulated in a dual layer capsule comprising an inner layer comprising the stem cell and a photoinitiator, and an outer layer comprising a hydrogel and substantially surrounding the inner layer.

In a further embodiment of the present invention, the photoinitiator is anchored to the stem cell.

In another embodiment of the present invention, the photoinitiator is eosin isothiocyanate.

In a further embodiment of the present invention, the hydrogel is gelatin methacrylate (gelMA) and polyethylene glycol diacrylate (PEGDA) hybrid hydrogel.

In one embodiment of the present invention, the cell is selected form the group consisting of jurkats or A549 cells.

In another embodiment of the present invention, the stem cell is selected from the group consisting of: a mesenchymal linear stem cell (MLC), a hematopoietic stem cell (HSC), and an endothelial progenitor cell (EPC).

In a further embodiment of the present invention, the photoinitiator is eosin-isothiocyanate and wherein the hydrogel is a gelatin methacrylate (gelMA) and polyethylene glycol diacrylate (PEGDA) hybrid hydrogel, and wherein the stem cell is selected from the group consisting of: a mesenchymal linear stem cell (MLC), a hematopoietic stem cell (HSC), and an endothelial progenitor cell (EPC).

In another embodiment of the present invention, the photoinitiator is eosin-isothiocyanate and anchored to the cell, wherein the hydrogel is a gelatin methacrylate (gelMA) and polyethylene glycol diacrylate (PEGDA) hybrid hydrogel, and wherein the stem cell is selected from the group consisting of: a mesenchymal linear stem cell (MLC), a hematopoietic stem cell (HSC), and an endothelial progenitor cell (EPC).

In one embodiment of the present invention, the method improves retention of a stem cell at an in vivo site of injury comprising injecting a therapeutic amount of a stem cell encapsulated in a dual layer capsule comprising an inner layer comprising the stem cell and a photoinitiator, and an outer layer comprising a hydrogel and substantially surrounding the inner layer, to the site of injury.

In another embodiment of the present invention is a method for improving the retention of a cell at an in vivo site of injury comprising injecting a therapeutic amount of a cell encapsulated in a dual layer comprising an inner layer comprising the cell and a photoinitiator, and an outer layer comprising a hydrogel and substantially surrounding the inner layer.

In a further embodiment of the present invention, the site of injury is in the myocardium.

In another embodiment of the present invention, the organ is in the heart.

In a further embodiment of the present invention, the site of injury is the endothelium.

BRIEF DESCRIPTION OF THE DRAWINGS

Illustrative aspects of embodiments of the present invention will be described in detail with reference to the following figures wherein:

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

Figure 1:
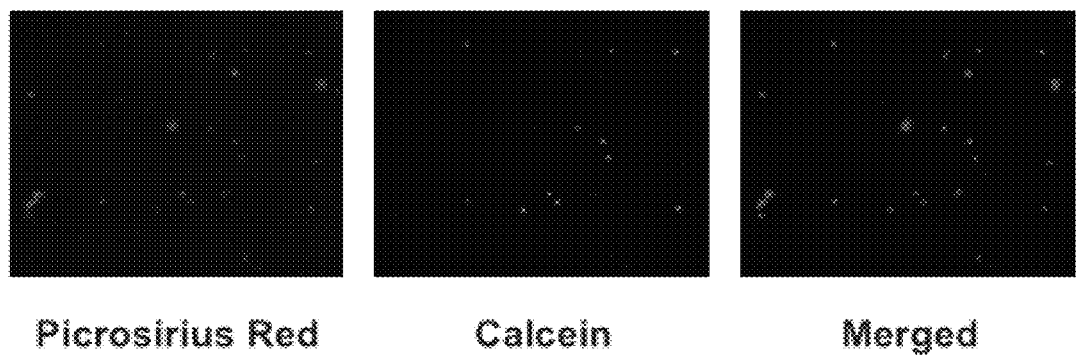
Figure 1:
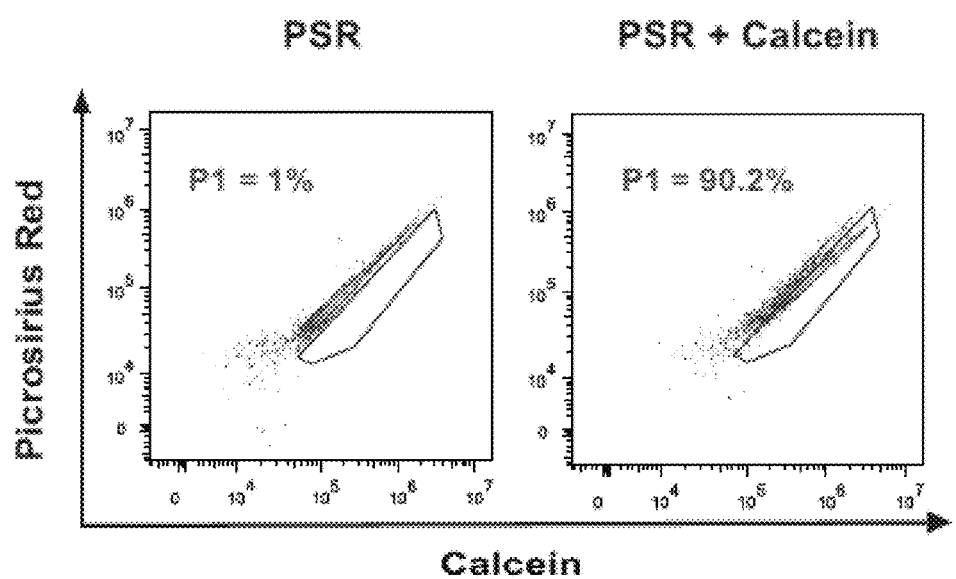

The presently-disclosed subject matter will be better understood, and features, aspects and advantages other than those set forth above will become apparent when consideration is given to the following detailed description thereof. Such detailed description makes reference to the following drawings, wherein:

FIG. 1 shows bone marrow cells remained alive after coating with polymer. Coated cells were identified with Picosirius red and live cells were identified by calcein. Cells were observed by immunofluorescence (A). Coated cells (red) that were live (green) appeared as orange when the two channels were merged. Cells were also visualized by flow cytometry (B). The red box identifies the region populated by live coated cells. The right panel shows coated cells stained with both Picosirius red and calcein while in the left panel, as a control, calcein was left out.

Figure 2:
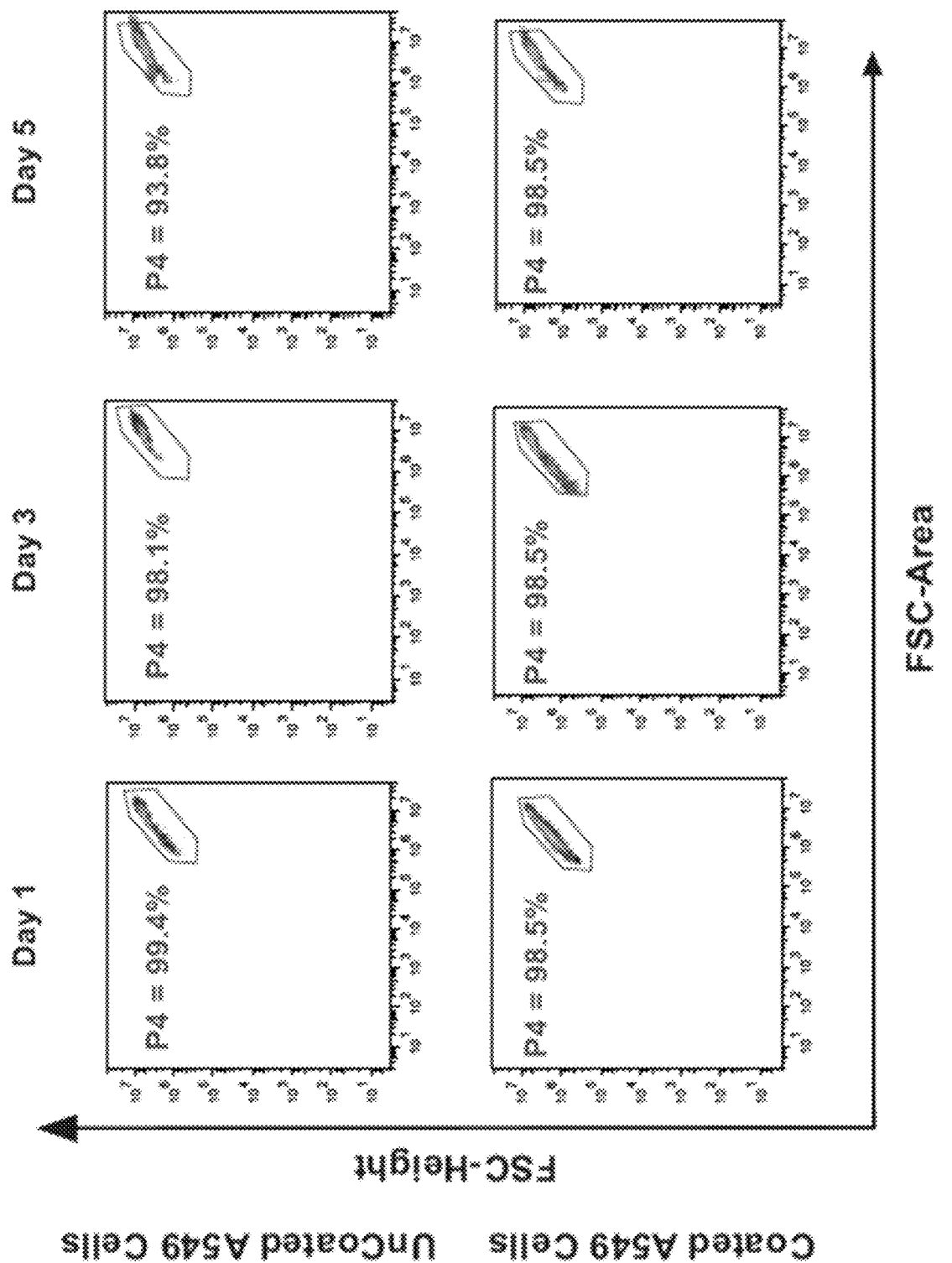

FIG. 2 coating did not predispose cells to aggregate. Coated and uncoated control A549 lung carcinoma cells were cultured for up to five days. Unstained cells were subjected to flow cytometry on Days 1, 3, and 5. Events falling outside the diagonal of forward scatter area versus height were considered to be aggregates. On forward scatter plots, where the area under the curve is plotted against the maximum height of the curve for each event, single cells fall along the diagonal, indicated by P4. A certain proportion of coated A549 cells are found outside P4, but since a similar proportion are found in the uncoated cultures, this aggregation is a natural phenomenon of this cell line.

Figure 3:
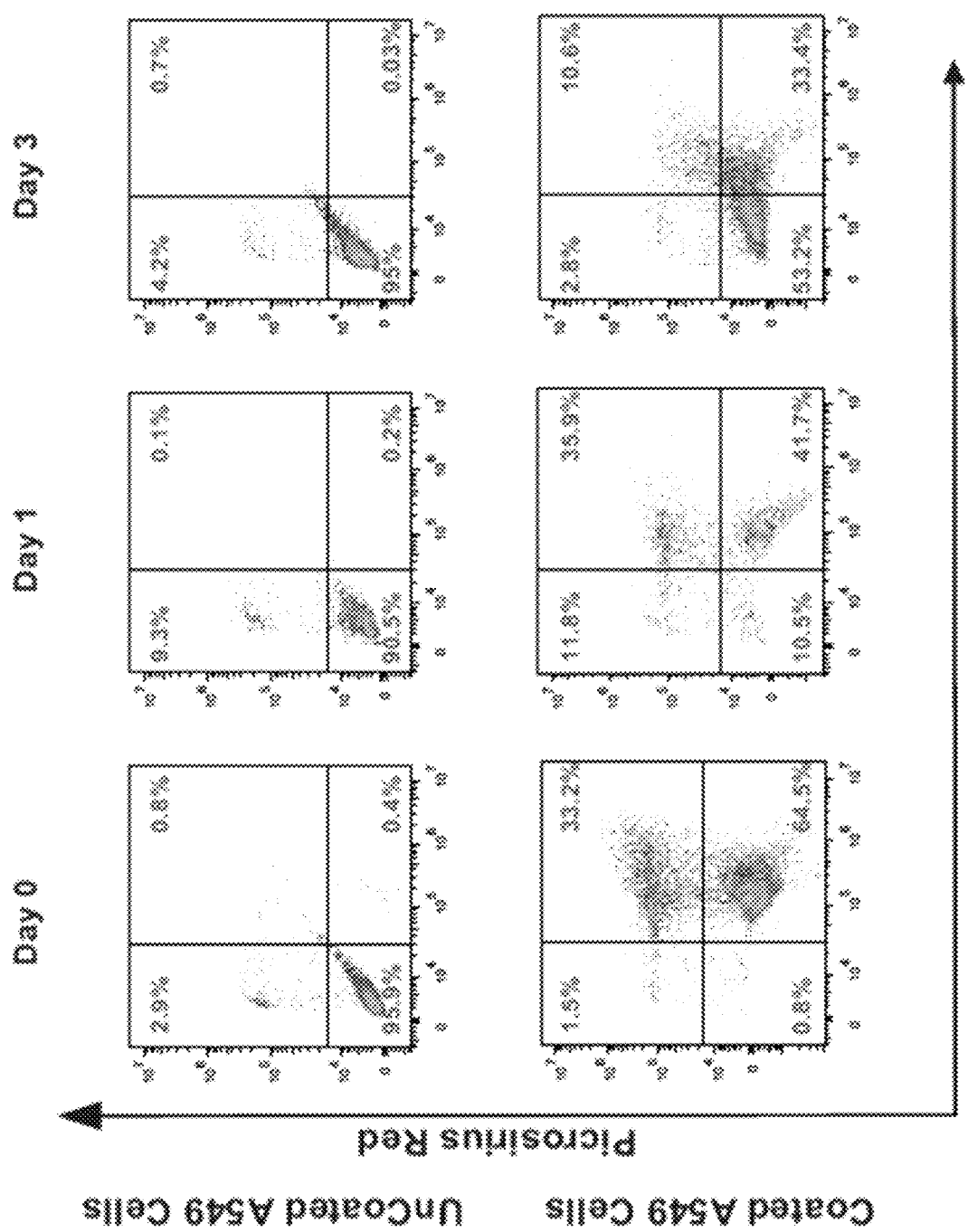

FIG. 3 cell coating began to degrade in vitro within 24 hr. Coated and uncoated control A549 lung carcinoma cells were cultured for up to three days. Coated cells were identified with Picosirius red. The fluorescence in the FL-1 channel of the coated cells was due to the presence of eosin, which was used to initiate polymerization. The plots demonstrate the progressive loss of coating on cultured cells over time.

Figure 4:
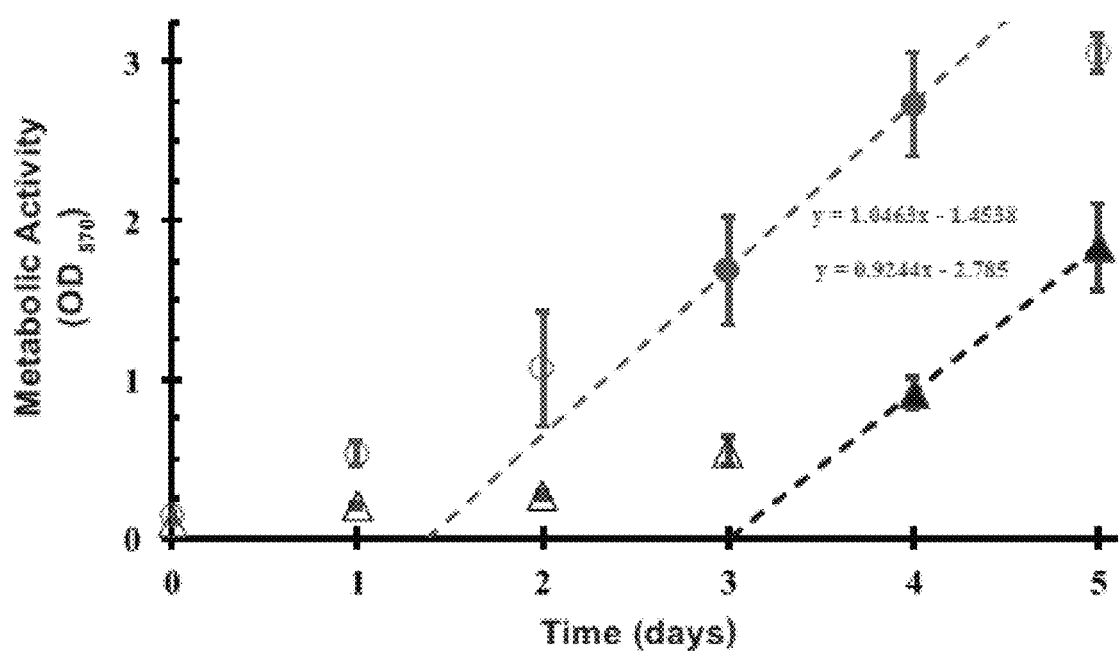

FIG. 4 shows coated A549 cells were metabolically active. Coated and control uncoated cells were cultured for up to five days in vitro. Each day, cultures of cells were assessed for metabolic activity by the MTT assay. After the initial lag phase, the metabolic activity of the coated cells was comparable to that of the control uncoated cells. Plot depicts a linear fit.

Figure 5:
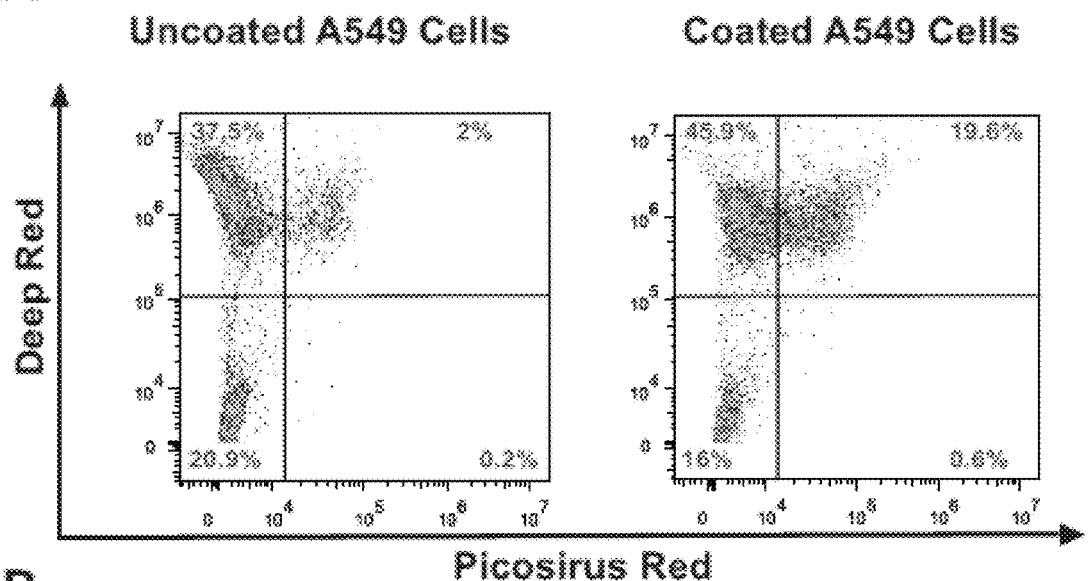
Figure 5:
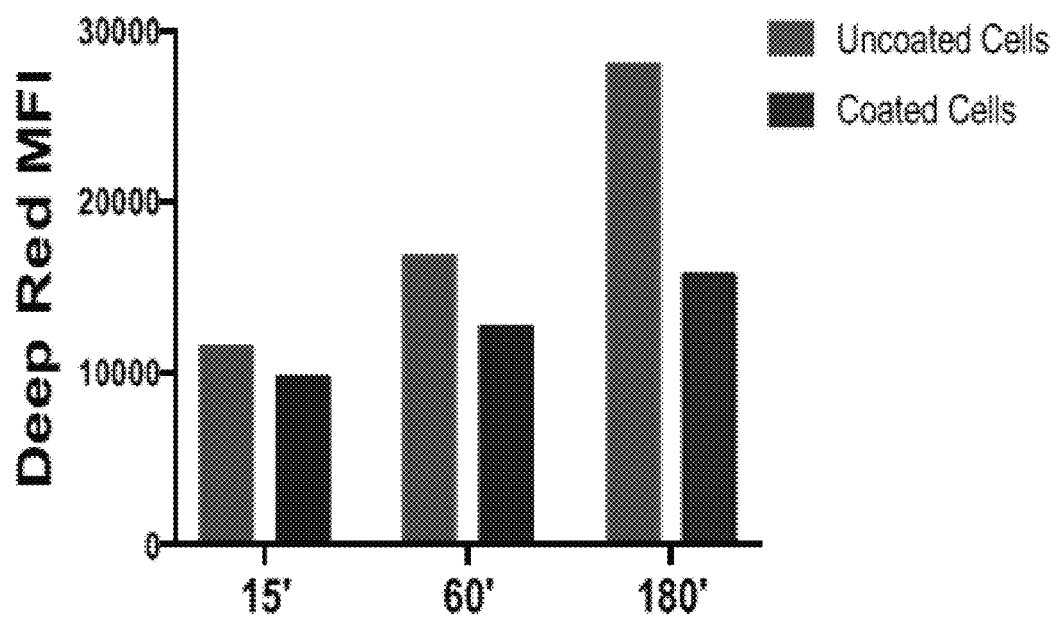

FIG. 5 shows coating does not predispose coated cells to be engulfed by macrophages. All A549 target cells were labeled with Deep Red while coated cells were identified by Picosirius Red. Target cells were cultured with unlabeled RAW264.7 macrophage effector cells for 15 minutes. Effector cells that had engulfed target cells were found in the lower left region (Panel A). Fewer professional phagocytes were present when coated A549 cells were co-cultured (right plot) than uncoated cells (left plot). The brightness of deep red, an indication of engulfment, was plotted for cultures indicating that coating may protect target cells from engulfment as detailed in the quantitative assessment of plots (Panel B).

Figure 6:
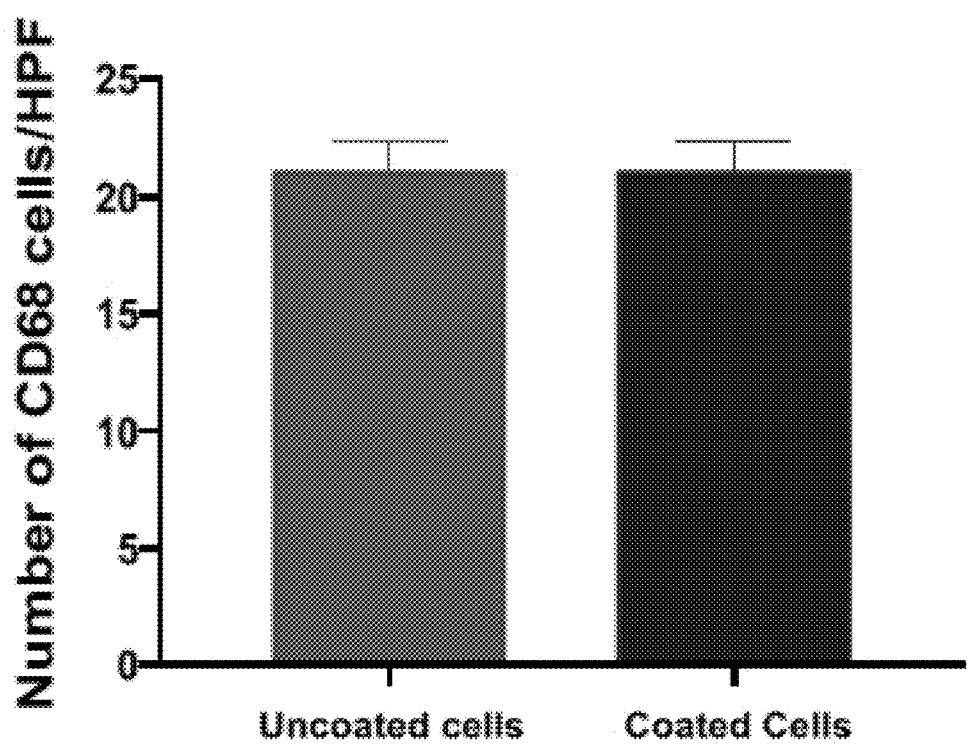

FIG. 6 shows the coating on the cells did not induce a localized inflammatory response. Paraffin imbedded sections were stained for CD6 and quantified as number of cells per power field were quantified. Quantitative analysis did not show significant difference between mice treated with coated or uncoated cells (N=3 mice/group).

Figure 7:
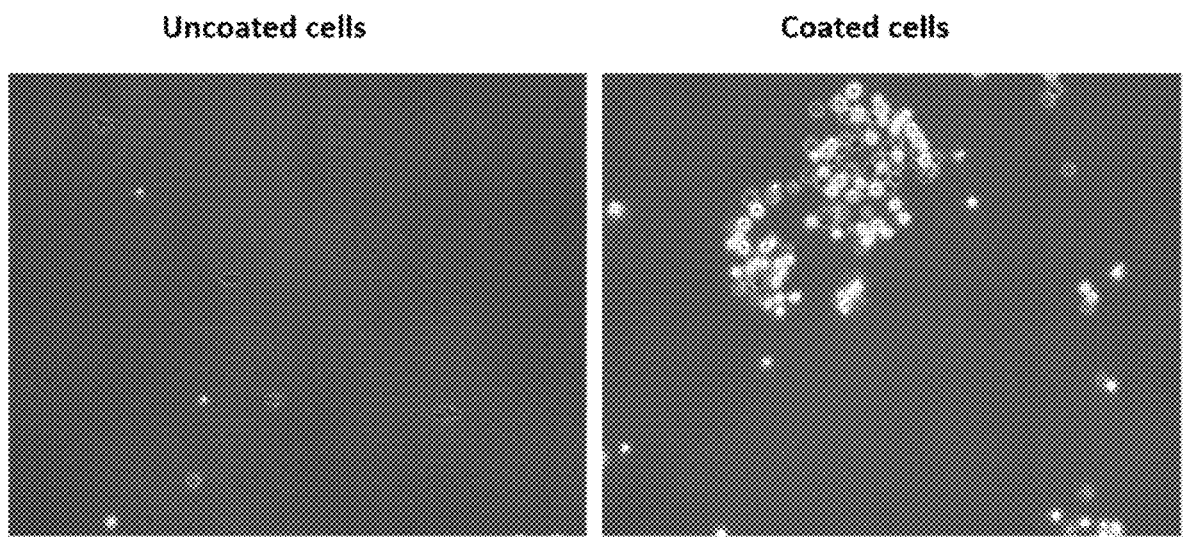

FIG. 7 shows coated cells have better retention on fibronectin under shear flow. Optical micrographs of fibronectin coated microscope slides contacted with polymer coated and uncoated Jurkat cells in phosphate buffer. Shearing flow of phosphate buffer imposed with a syringe pump and a microfluidic device.

Figure 8:
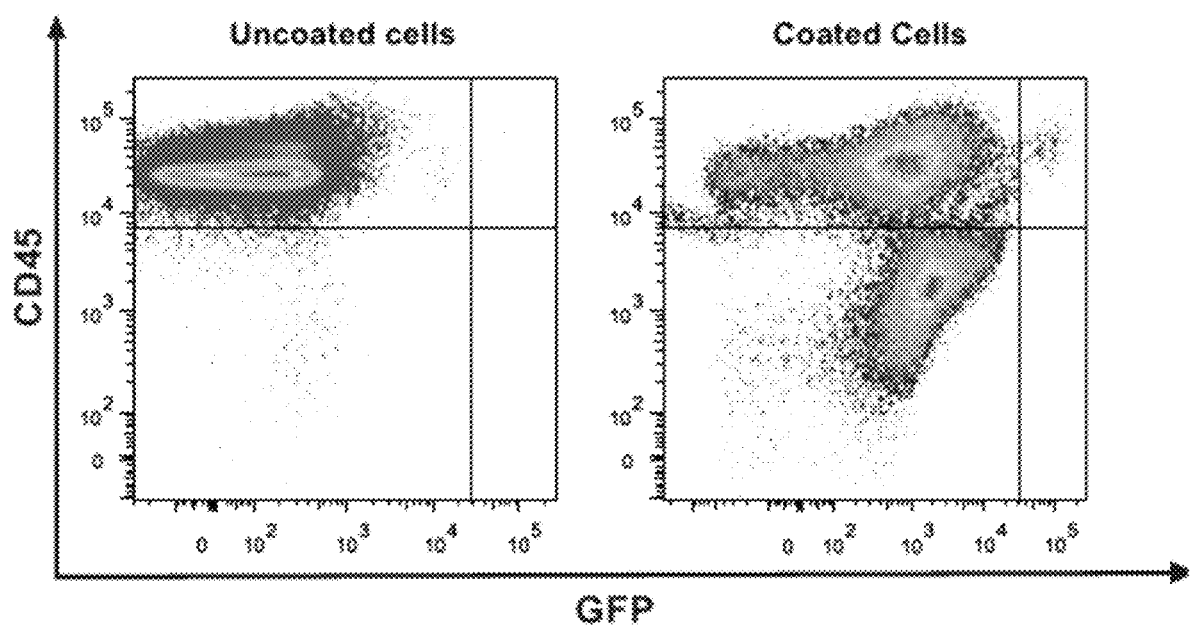
Figure 8:
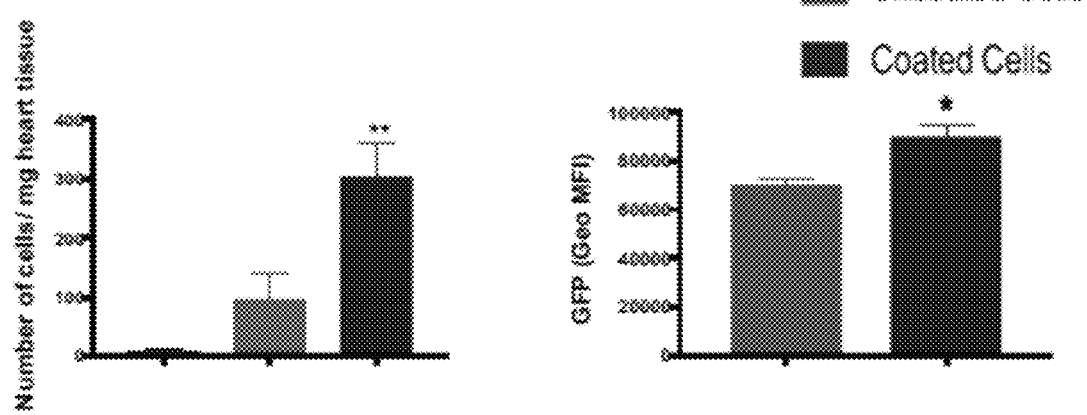
Figure 8:
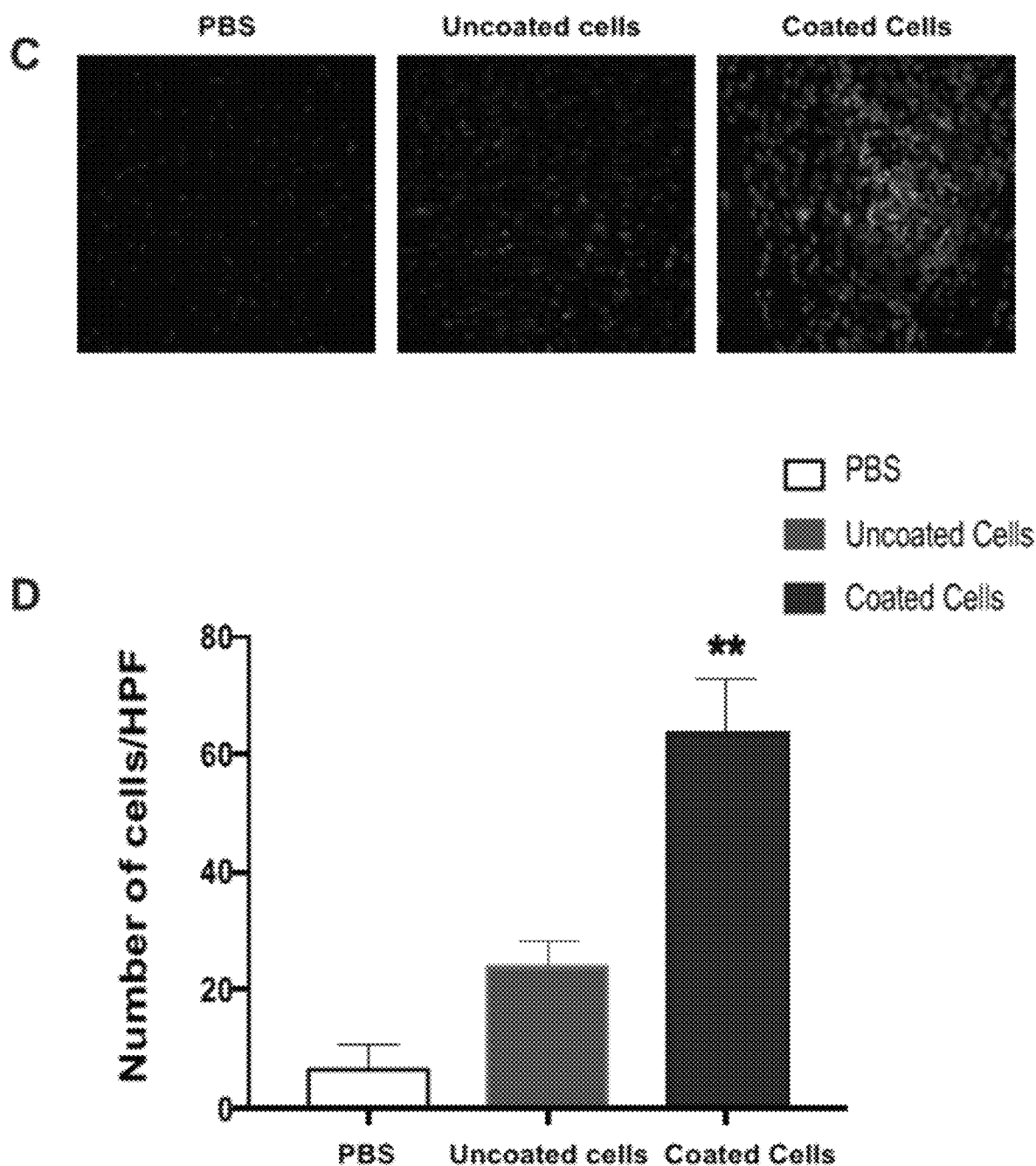
Figure 8:
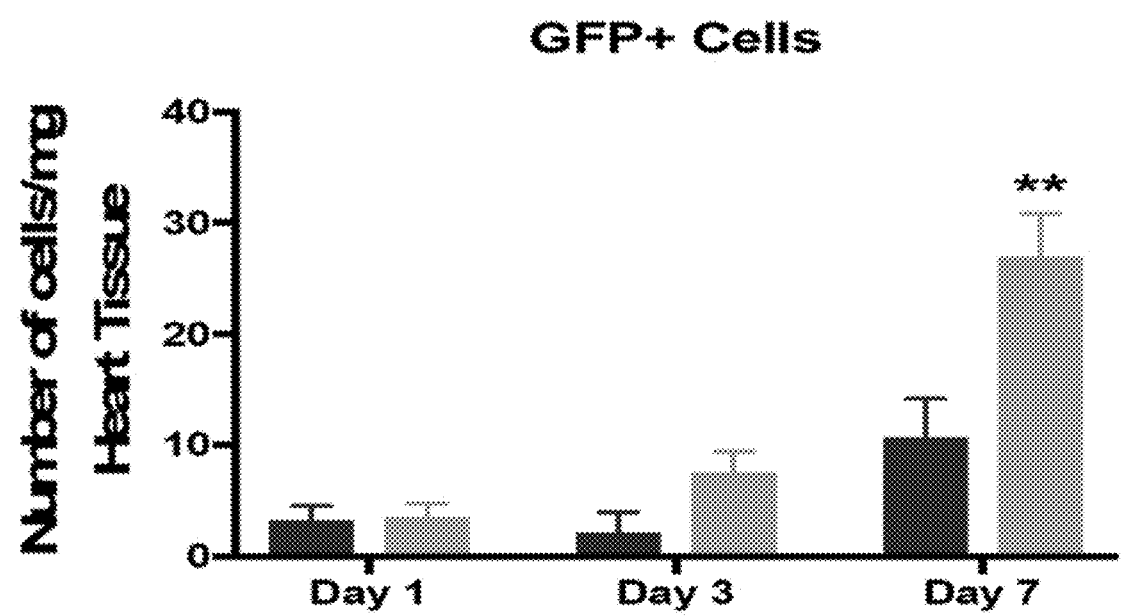

FIG. 8 shows coated cells were more efficiently retained in the heart. Flow cytometry analyses of digested heart tissue demonstrate higher percentage of GFP+ cells in mice treated with coated cells comparted to mice transplanted with uncoated cells. Panel A shows the expression of CD45 and GFP in digested heart tissue where the majority of GFP cells were CD45+. Panel B illustrates a quantitative analysis of GFP+ cells in digested heart tissue of mice treated with coated and uncoated bone marrow cells showing higher percentage of GFP+ cells in mice treated with coated bone marrow cells. Immunohistochemical analysis demonstrated higher numbers of retained GFP+ bone marrow cells in mice treated with coated cells (Panel C). Quantitatively, mice treated with coated cells exhibited higher numbers for GFP+ cells per high power field as compared to mice treated with uncoated cells (Panel D) (N=3 mice/group; *P<0.05, **P<0.01). Panel E shows a quantitative analysis of coated and uncoated GFP+ Mesenchymal Stem Cells retained in mice heart (N=4 mice).

Figure 9:
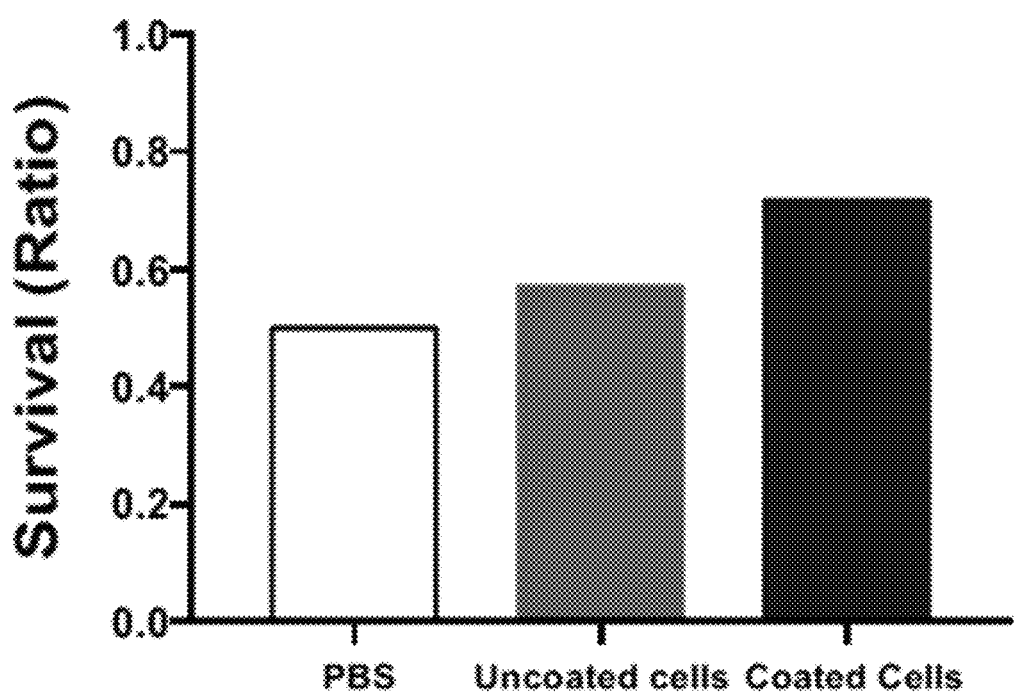

FIG. 9 shows coated cells improved short term survival over uncoated cells. Mice transplanted with coated bone marrow cells had a higher survival rate by seven days post myocardial infarction compared to those mice transplanted with uncoated cells or PBS only (N=8 mice/group).

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, and in some embodiments ±0.01% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein, the term "subject" refers to a target of administration. The subject of the herein disclosed methods can be a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A "patient" refers to a subject afflicted with a disease or disorder. The term "patient" includes human and veterinary subjects.

As used herein, the term "treatment" refers to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. Such a diagnosis can be in reference to a disorder, such as cardiovascular disease, and the like, as discussed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "photoinitiator" refers to a compound capable of receiving light energy and initiating polymerization of polymerizable materials. A photoinitiator may be classified as a compound capable of absorbing light energy and converting the light energy into chemical energy typically by creating free radicals or cations. Light energy may be in the ultraviolet, visible, or infrared spectrum. Photoinitiators can undergo a unimolecular bond cleavage upon radiation yielding free radicals or undergo a biomolecular reaction where the excited state of the photoinitiator interacts with a second (co-initiator) molecule to generate free radicals. A person having ordinary skill in the art can easily recognize general classes of certain photoinitiators as benzoin ethers, benzyl ketals, alpha-dialkoxyacetophenones, alpha-hydroxyalkylphenones, alpha-aminoalkylphenones, acyl-phosphine oxides, benzophenones, benzoamines, thioxanthones, thioamines, xanthenes, or titanocenes. Photoinitiators may also include fluorescent and phosphorescent compounds. While any one skilled in the art will readily recognize photoinitiators suitable for the present invention, specific examples of photoinitiator compounds include eosin, eosin 5-isothiocyanate, and fluorescein.

As used herein, "anchor," "anchored" or "anchoring" refers to a reversible or non-reversible link between two entities. The two entities may be the same or different and may be selected from: chemical compounds, proteins, peptides, cells, nucleic acids, or conjugates thereof. Anchoring may be direct or mediated through molecules that possess ideal affinity for each other. One example of such molecules used for anchoring purposes is the avidin (or streptavidin)- biotin molecular interaction whereby one entity is labeled with streptavidin and a second entity is labeled with biotin. By way of the streptavidin-biotin interaction, one entity is then anchored to the other.

As used herein, the term "effective amount" refers to an amount that is sufficient to achieve the desired result or to have an effect on an undesired condition. For example, the term "therapeutically effective amount" refers to an amount that is sufficient to achieve the desired therapeutic result or to have an effect on undesired symptoms, but is generally insufficient to cause adverse side effects. The specific therapeutically effective dose level for any particular subject will depend upon a variety of factors including the disorder being treated and the severity of the disorder; the specific composition employed; the age, body weight, general health, sex and diet of the subject; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

EXAMPLES

Materials & Methods

Study Design. Male C57BL/6 WT and C57BL/6-Tg (CAG-EGFP)131Osb/LeySopJ mice (Jackson Laboratory, BarHarbor, Me.), aged 8-10 weeks, were used in the present invention. All procedures were conducted under the approval of the University of Kentucky IACUC in accordance with the NIH Guide for the Care and Use of Laboratory Animals (DHHS publication No. [NIH] 85-23, rev. 1996). A549 (human epithelial lung carcinoma), RAW264.7 (mouse macrophage cell line), and Jurkat (T lymphocyte) cells were obtained from ATCC.

Murine Model of Myocardial Infarction. Mice were anesthetized with 1-3% isoflurane using an inhaled delivery system. The heart was exposed, pushed out of the thorax with a direct visual control and the left anterior descending coronary artery (LAD) was sutured and ligated at a site approximately 3 mm from its origin using a 6-0 silk suture as previously described [18, 19].

Cell encapsulation. Cells were washed twice with PBS by centrifuging each time at 500×g, 3 minutes at 4° C. 1.5×10$^6$ cells were collected for each polymerization trial. PBS buffer was removed, and the cell pellet was resuspended in 200 µL of 1 mM Biotin sulfo NHS (Thermo Fisher Scientific, Waltham, Me.) in PBS and incubated for 40 minutes on ice. Following incubation, 800 µL of PBS was added and rinsed twice by centrifuging at 500×g for 3 minutes at 4° C. The cell pellet was then resuspended in 1 mL of PBS containing 35 µg/mL streptavidin-eosin isothiocyanate and incubated for 30 minutes on ice. Streptavidin (Thermo Fisher Scientific, Waltham, MA) and eosin-5-isothiocyanate (Sigma Aldrich, St. Louis, Mo.) conjugation was made in-house as described by Hansen et al. After 30 minutes of incubation, the cells were washed twice in PBS by centrifuging at 500×g for 3 minutes at 4° C. The polymer mixture buffer was prepared using 35 mM triethanol amine and 35 mM 1-vinyl-2-pyrrolidinone in PBS. This mixture was purged with ultra-pure N2 for 10 minutes. 3 wt % gelatin methacrylate (gelMA) (BioBots, Philadelphia, Pa.) was added to the buffer and vortexed and sonicated for 10 minutes. 1 wt % PEGDA 3500 (JenKem Technology, Plano, Tex.) was then added to the 3 wt % gelMA solution and vortexed. The final polymer mixture was filtered through a 0.2 μm mesh syringe filter and stored at RT. 350 μL of the polymer mixture was added to the cell pellet and gently vortexed and loaded into a chip-clip well (Whatman) with a standard microscopy slide. The chip-clip was incubated in dark for 3 minutes before placing into a N2 purged sealed plastic clear zip lock bag. The cells were polymerized for 10 minutes at 30 mW/cm2 under 530 nm green visible light while purging with N2. After 10 minutes, the slide was washed twice with 1 ml of PBS each time.

Flow Cytometry. Heart tissue was harvested at 7 days and placed in ice cold PBS instantly. Heart tissue was minced then digested using a collagenase B (Roche, Indianapolis, Ind.) and dispase II (Roche, Indianapolis, Ind.) solution for 30 minutes at 37° C. with mixing every 5 minutes.

The enzymatic reaction was stopped by dilution with Flow Buffer (PBS+5% normal goat serum+0.1% sodium azide) and the heart cell suspensions were passed through 40 μm strainers. Cells were centrifuged at 400×g for 5 min at 4° C., then suspended in Flow Buffer. Cells were incubated directly for 30 minutes with eFluor 660 conjugated GFP Antibody Clone 5F12.4 (eBioscience, Thermo Fisher Scientific, Waltham Mass.) and APC-CY7-conjugated CD45 (Biolegend, San Diego Calif.). After incubation, cells were washed twice using flow buffer and analyzed using an LSR II (Becton Dickinson) in the University of Kentucky Flow Cytometry Core. Laser calibration and compensation were carried out utilizing unstained and single fluorescent control beads (eBioscience). FlowJo v7 was used (FlowJo, FlowJo Ashland Oreg.) software to generate dot plots and analyze the data.

Immunohistochemistry. Immunohistochemical assessments were carried out on de-paraffinized and rehydrated sections as previously described [19]. Briefly, sections were exposed to heat-mediated epitope retrieval in citrate buffer, pH 6.0 (Vector Laboratories, Burlingame Calif.)) for 20 mins, then blocked with normal goat serum for 10 minutes at 37° C. Slides were incubated with primary antibodies: rabbit anti-GFP (Abcam, Cambridge, United Kingdom) or rat anti-mouse CD68 (Abcam). After washing, sections were incubated with secondary antibodies conjugated to APC or FITC, respectively. The sections were finally incubated with Sudan Black B (Sigma Aldrich, St. Louis, Mo.) for 30 minutes. Adjacent areas in the pre-infarct and remote zones were analyzed (1 section/animal, n=2 animals/group) at 40× magnification using Nikon Confocal Microscope A1 (Nikon, Tokyo, Japan) in the University of Kentucky Confocal Microscopy facility. Calculations were performed using the Cell Counter plugin for ImageJ, version 1.51d (NIH, Rockville, Md.).

Microfluidic shear assay. Fibronectin coated substrates were prepared by allowing a 1 mg/mL solution of fibronectin to dry overnight on an epoxy-coated microscope slide (CEL Associates). Slides were rinsed with phosphate buffer immediately prior to use. Coated cells were prepared as described above. Coated or uncoated Jurkats were incubated on the fibronectin surfaces for 40 minutes. Following incubation, the slide was mounted to a parallel plate flow chamber (GlycoTech) with a gasket thickness of 0.01 in. Buffer was passed through the assembled device using a syringe pump at a flow rate of 40 mL/min. Micrographs were collected before and after flow using a phase contrast objective on a Nikon Ti-U inverted optical microscope.

Engulfment assay. Coated and uncoated target A549 cells were labeled with MitoTracker Deep Red (Invitrogen, Thermo Fisher Scientific) according to the manufacturer's protocol. The target cells were then cultured with effector RAW264.7 cells that had been seeded the previous day in 6 well plates. Cultures were removed with the help of a cell scraper, washed with PBS, and then subjected to flow cytometry.

Statistical Analysis. Values are expressed as mean±standard error of mean (SEM). Unpaired Student t-test or analysis of variance (one-way or multiple comparisons) were used to estimate differences, as appropriate. Two-sided Dunnett or Dunn tests were used for post hoc multiple comparison procedures, with control samples as the control category. Throughout the analyses, a p value less than 0.05 was considered statistically significant. All statistical analyses were performed using the Prism 7 software package (GraphPad, La Jolla, Calif.).

Results

Bone marrow derived cells remain viable after coating with gelatin methacrylate biodegradable polymer. Prior studies documented the ability to generate biosynthetic polymer coating on living cells. These coatings were designed using polyethylene glycol (PEG) based polymers to completely coat cells for purification purposes [16]. PEG based coatings allow essential nutrient transport thus preserving cell viability [17]. Gelatin methacrylate biodegradable coating was used to achieve improved cell adhesion and retention in cardiac tissue. Picosirius red was integrated in the polymer to identify coated cells (FIG. 1A). Gelatin methacrylate coated BMCs were viable as assessed by histological and flow cytometric techniques (FIG. 1). On average, ~60% coating and 85% of coated cells appeared to be viable based on calcein viability staining.

Coated bone marrow derived cells do not aggregate. Cell coating can be of great benefit in stem cell based studies, especially in cardiac applications. However, cell aggregation can be detrimental in certain delivery methods such as intracoronary infusion where aggregated cells can block microvasculature leading to myocardial infarction. Further studies were conducted to rule out the possibility that monomers on two adjacent cells do crosslink resulting in cell-cell aggregates. To determine what impact, if any, the cell coating had on cell-cell aggregates, the number of aggregates was quantified in A549, a human lung carcinoma cell line. A549 cells were either coated or left uncoated and then cultured for up to five days in RPMI with 10% FBS. Using flow cytometry, the cell aggregates were analyzed using the forward scatter height and area. The analyses did not show a significant difference in cell aggregates between coated and uncoated cells during up to 5 days of culture (FIG. 2). Therefore, the data shows that neither the process of polymerization nor the coating itself had a significant impact on cell-cell aggregation.

Gelatin based cell coatings are degradable. In clinical applications, a cell coating is ideally degradable allowing stem cells to exert their beneficial effects after the resolution of inflammation. This is particularly important during the early inflammatory phase that peaks at 72 hours after MI [20-22]. Hence, the gelatin methacrylate coating to degrade naturally within 72 hours. The gelatin coatings are naturally degraded by MMPs. While bone marrow cells express low levels of MMP activity, the ischemic heart expresses high levels of MMPs [23]. To demonstrate that coated cells are capable of degrading their gelatin coating, cells were coated that have high level of MMP secretion capability (A549 cells) and cultured them for three days in RPMI+10% FBS medium under normal culture conditions. Cell coating was confirmed using Picosirius red which was assessed by flow cytometry (FIG. 3). Within one day of culturing, there was a reduction in the amount of coating on cells which further decreased by Day 3. Additionally, in in vivo studies, coating in immunohistochemistry studies was not observed. Taken together, findings suggest that the gelatin coating is transient and can be degraded to release cells to exert their therapeutic effect after transplantation.

Coated A459 cells remain metabolically active in vitro. Prior studies demonstrated that a PEG based biosynthetic cell coating is compatible with nutrient transfer. It was then necessary to determine if cells coated with the gelatin-based biodegradable material remained metabolically active. Coated and uncoated A549 cells were cultured for up to five days in normal culture conditions. Immediately after coating and every day afterwards, cells were harvested and their metabolic activity was measured by the MTT assay. Initially, the coated cells expressed lower metabolic activity as compared to uncoated controls. However, by Day 3, the MTT assay showed equivalent activity between coated and uncoated cells as both lines had similar slopes (FIG. 4). The MTT assay indicated a lag of approximately a day and a half in the coated cells. This lag could be explained, at least in part, by the delayed attachment of coated cells which required an additional one to one and half days to adhere to the surface of the plate compared to uncoated cells.

Coated bone marrow derived cells do not elicit an immune response. While cell coating could provide cell protection from inflammatory conditions, the possibility of coating triggering an immune response needs to be excluded. A cell tracking system was used where all cells (coated and uncoated) were incubated with Mitotracker Deep Red. The target A549 cells were cultured with mouse RAW264.7 macrophage effector cells at a ratio of 5:1 for 15 minutes. Effector cells that had engulfed target cells acquired Deep Red from the target cells and then expressed a low level of Deep Red (FIG. 5A). Fewer effector cells (RAW264.7 macrophage) expressing the Mitotracker Deep Red dye were observed when incubated with the coated than with uncoated cells. On the other hand, no effector cells expressing Deep Red dye when effector cells were cultured without target cells confirming the specificity of the approach (data not shown). Using MFI analysis and the brightness of Deep Red as an indication of engulfment, less coated cells were observed being engulfed by RAW264.7 macrophage effector cells than uncoated cells. This pattern was observed for up to 3 hours of co-culture (FIG. 5B).

Cell coating does not elicit an immune response in the heart using in vivo studies. heart sections were stained 7 days after MI and cell transplantation against CD68 marker of macrophages. The number of CD68+macrophages was similar in the hearts of mice injected with coated bone marrow cells compared to control uncoated cells (FIG. 6) implying that the coating did not enhance the inflammatory response seen upon MI.

Polymer coated cells adhere strongly to ECM surfaces. Having determined that coated cells remained alive, meta- bolically active and did not elicit an immune response, their in vitro retention was investigated on model ECM substrates while being subjected to shear flow. Coated or uncoated Jurkat cells were incubated on a fibronectin coated microscope slide for 40 minutes. Following incubation, a parallel plate flow chamber (Glycotech) was fitted to the slide, and the cells were imaged before and after a 5 minute exposure to a shearing flow of phosphate buffer (40 mL/minute, ~56 dyne/cm2). The retention of cells was observed by optical microscopy (FIG. 7). The uncoated cells were largely rinsed from the fibronectin surface, while the adhesion of the polymer coated cells to the surface was sufficient to retain many of the cells on the substrate.

Polymer coated cells demonstrate enhanced retention in the heart following transplantation. Cell retention was next investigated in the heart was investigated after acute myocardial infarction. Immediately after WT BL/6 mice were subjected to MI using the LAD permanent model, and $3 \times 10^6$ unfractionated bone marrow cells from GFP mice were injected in two separate peri-infract locations. The use of GFP donor cells allows us to track the retention and fate of transplanted cells. Seven days later, the number of BMCs retained in the heart was examined using immunohistochemistry and flow cytometry. Hearts were isolated, digested to single cell suspension then stained against CD45 and GFP. significantly higher numbers of GFP+BMCs with the coated arm compared to PBS arm and uncoated cells (PBS=7.5±4.3 vs. uncoated=96.5±45.3 vs. coated=302±58.9 cells/mg heart tissue, P=0.0017) was observed (FIGS. 8A and B). The immunohistochemistry data confirmed these findings with the location of GFP cells in mice transplanted with coated cells compared to those transplanted with uncoated cells or treated with PBS (PBS=6.5±4.2 vs. uncoated=23.8±4.3 vs. coated=63.4±9.5 cells/high power field, P<0.001). GFP+ cells were observed primarily in the peri-infarct region (FIGS. 8C and D). Similar results were seen when coated mesenchymal stem cells were injected after acute MI (FIG. 8E). Interestingly, coated bone marrow cells had a higher expression of GFP on flow cytometry, supporting their viability.

The enhanced retention of BMCs in the heart after MI was associated with increased survival. At 7 days after MI, mice treated with coated BMCs experienced 71% survival compared to mice treated with uncoated BMCs (57%) and mice treated with PBS (50%) (FIG. 9).

REFERENCES

All publications, patents, and patent applications mentioned in this specification are herein incorporated by reference to the same extent as if each individual publication, patent, or patent application was specifically and individually indicated to be incorporated by reference, including the references set forth in the following list:

1. Moran, A. E., et al., *Temporal Trends in Ischemic Heart Disease Mortality in 21 World Regions, 1980-2010: The Global Burden of Disease 2010 Study*. Circulation, 2014.
2. Kiessling, A. and P. Henriksson, *Time trends of chest pain symptoms and health related quality of life in coronary artery disease*. Health and quality of life outcomes, 2007. 5(1): p. 13
3. Asahara, T., A. Kawamoto, and H. Masuda, *Concise Review: Circulating Endothelial Progenitor Cells for Vascular Medicine*. Stem Cells, 2011. 29(11): p. 1650-1655.

4. Hofmann, M., et al., *Monitoring of bone marrow cell homing into the infarcted human myocardium.* Circulation, 2005. 111(17): p. 2198-202.
5. Quyyumi, A., et al., *One year follow-up results from PRESERVE-AMI: a randomized, double-blind, placebo controlled clinical trial of intracoronary infusion of autologous CD34+ cells in patients with left ventricular dysfunction post STEMI.* J Am Coll Cardiol, 2015. 55(10): p. A1593.
6. Afzal, M. R., et al., *Adult Bone Marrow Cell Therapy for Ischemic Heart Disease: Evidence and Insights from Randomized Controlled Trials.* Circ Res, 2015.
7. Kavanagh, D. P., J. Robinson, and N. Kalia, *Mesenchymal stem cell priming: fine-tuning adhesion and function.* Stem Cell Rev, 2014. 10(4): p. 587-99.
8. Zhou, Y., et al., *Effects of Human Fibroblast-Derived Extracellular Matrix on Mesenchymal Stem Cells.* Stem Cell Rev, 2016. 12(5): p. 560-572.
9. Arnaoutova, I., et al., *Basement membrane matrix (BME) has multiple uses with stem cells.* Stem Cell Rev, 2012. 8(1): p. 163-9.
10. Purcell, B. P., et al., *Synergistic effects of SDF-1alpha chemokine and hyaluronic acid release from degradable hydrogels on directing bone marrow derived cell homing to the myocardium.* Biomaterials, 2012. 33(31): p. 7849-57.
11. MacArthur, J. W., Jr., et al., *Sustained release of engineered stromal cell-derived factor 1-alpha from injectable hydrogels effectively recruits endothelial progenitor cells and preserves ventricular function after myocardial infarction.* Circulation, 2013. 128(11 Suppl 1): p. S79-86.
12. Liu, G., et al., *A VEGF delivery system targeting MI improves angiogenesis and cardiac function based on the tropism of MSCs and layer-by-layer self-assembly.* Biomaterials, 2017. 127: p. 117-131.
13. Nash, M. E., et al., *Thermoresponsive substrates used for the expansion of human mesenchymal stem cells and the preservation of immunophenotype.* Stem Cell Rev, 2013. 9(2): p. 148-57.
14. Sarig, U. and M. Machluf, *Engineering cell platforms for myocardial regeneration.* Expert Opin Biol Ther, 2011. 11(8): p. 1055-77.
15. D'Souza, S., et al., *Engineering of cell membranes with a bisphosphonate-containing polymer using ATRP synthesis for bone targeting.* Biomaterials, 2014. 35(35): p. 9447-58.
16. Romero, G., et al., *Protective Polymer Coatings for High-Throughput, High-Purity Cellular Isolation.* ACS Appl Mater Interfaces, 2015. 7(32): p. 17598-602.
17. Lilly, J. L., et al., *Characterization of molecular transport in ultrathin hydrogel coatings for cellular immunoprotection.* Biomacromolecules, 2015. 16(2): p. 541-9.
18. Gao, E., et al., *A novel and efficient model of coronary artery ligation and myocardial infarction in the mouse.* Circ Res, 2010. 107(12): p. 1445-53.
19. Klyachkin, Y. M., et al., *Pharmacological Elevation of Circulating Bioactive Phosphosphingolipids Enhances Myocardial Recovery After Acute Infarction.* Stem Cells Transl Med, 2015.
20. Nahrendorf, M., et al., *The healing myocardium sequentially mobilizes two monocyte subsets with divergent and complementary functions.* J Exp Med, 2007. 204(12): p. 3037-47.
21. van der Laan, A. M., et al., *Monocyte subset accumulation in the human heart following acute myocardial infarction and the role of the spleen as monocyte reservoir.* Eur Heart J, 2014. 35(6): p. 376-85.
22. Epelman, S., P. P. Liu, and D. L. Mann, *Role of innate and adaptive immune mechanisms in cardiac injury and repair.* Nat Rev Immunol, 2015. 15(2): p. 117-29.
23. Peterson, J. T., et al., *Evolution of matrix metalloprotease and tissue inhibitor expression during heart failure progression in the infarcted rat.* Cardiovasc Res, 2000. 46(2): p. 307-15.
24. Ratajczak, M. Z., et al., *Pivotal role of paracrine effects in stem cell therapies in regenerative medicine: can we translate stem cell-secreted paracrine factors and microvesicles into better therapeutic strategies?* Leukemia, 2012. 26(6): p. 1166-73.
25. Wojakowski, W., et al., *Very small embryonic-like stem cells in cardiovascular repair.* Pharmacol Ther, 2011. 129(1): p. 21-8.
26. Zuba-Surma, E. K., et al., *Very small embryonic-like stem cells: biology and therapeutic potential for heart repair.* Antioxid Redox Signal, 2011. 15(7): p. 1821-34.
27. Losordo, D. W., et al., *Intramyocardial, autologous CD34+ cell therapy for refractory angina.* Circ Res, 2011. 109(4): p. 428-36.
28. Zuba-Surma, E. K., et al., *Transplantation of expanded bone marrow-derived very small embryonic-like stem cells (VSEL-SCs) improves left ventricular function and remodelling after myocardial infarction.* J Cell Mol Med, 2011. 15(6): p. 1319-28.
29. Brenner, W., et al., *111In-labeled CD34+ hematopoietic progenitor cells in a rat myocardial infarction model.* J Nucl Med, 2004. 45(3): p. 512-8.
30. Abbott, J. D., et al., *Stromal cell-derived factor-1alpha plays a critical role in stem cell recruitment to the heart after myocardial infarction but is not sufficient to induce homing in the absence of injury.* Circulation, 2004. 110 (21): p. 3300-5.
31. Kucia, M., et al., *CXCR4-SDF-1 signalling, locomotion, chemotaxis and adhesion.* J Mol Histol, 2004. 35(3): p. 233-45.
32. Marquez-Curtis, L. A., et al., *The ins and outs of hematopoietic stem cells: studies to improve transplantation outcomes.* Stem cell reviews, 2011. 7(3): p. 590-607.
33. McQuibban, G. A., et al., *Matrix metalloproteinase activity inactivates the CXC chemokine stromal cell-derived factor-1.* J Biol Chem, 2001. 276(47): p. 43503-8.
34. McQuibban, G. A., et al., *Matrix metalloproteinase processing of monocyte chemoattractant proteins generates CC chemokine receptor antagonists with anti-inflammatory properties in vivo.* Blood, 2002. 100(4): p. 1160-7.
35. Agarwal, U., et al., *Role of cardiac myocyte CXCR4 expression in development and left ventricular remodeling after acute myocardial infarction.* Circ Res, 2010. 107(5): p. 667-76.
36. Fedorovich, N. E., et al., *Hydrogels as extracellular matrices for skeletal tissue engineering: state-of-the-art and novel application in organ printing.* Tissue Eng, 2007. 13(8): p. 1905-25.
37. Hamidi, M., A. Azadi, and P. Rafiei, *Hydrogel nanoparticles in drug delivery.* Adv Drug Deliv Rev, 2008. 60(15): p. 1638-49.
38. Lin, C. C. and K. S. Anseth, *PEG hydrogels for the controlled release of biomolecules in regenerative medicine.* Pharm Res, 2009. 26(3): p. 631-43.
39. Blackburn, N. J., et al., *Timing underpins the benefits associated with injectable collagen biomaterial therapy for the treatment of myocardial infarction.* Biomaterials, 2015. 39: p. 182-92.

40. Holladay, C. A., et al., *Recovery of cardiac function mediated by MSC and interleukin-10 plasmid functionalised scaffold*. Biomaterials, 2012. 33(5): p. 1303-14.
41. Serpooshan, V., et al., *The effect of bioengineered acellular collagen patch on cardiac remodeling and ventricular function post myocardial infarction*. Biomaterials, 2013. 34(36): p. 9048-55.
42. Lilly, J. L. and B. J. Berron, *The Role of Surface Receptor Density in Surface-Initiated Polymerizations for Cancer Cell Isolation*. Langmuir, 2016. 32(22): p. 5681-9.
43. Lilly, J. L., et al., *Interfacial polymerization for colorimetric labeling of protein expression in cells*. PLoS One, 2014. 9(12): p. e115630.
44. Afzal, M. R., et al., *Adult Bone Marrow Cell Therapy for Ischemic Heart Disease: Evidence and Insights From Randomized Controlled Trials*. Circ Res, 2015. 117(6): p. 558-75.
45. Quyyumi, A. A., et al., *PreSERVE-AMI: A Randomized, Double-Blind, Placebo-Controlled* Clinical Trial of Intracoronary Administration of Autologous CD34+ *Cells in Patients With Left Ventricular Dysfunction Post STEMI*. Circ Res, 2017. 120(2): p. 324-331.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. An injectable composition to enhance cell retention at an in vivo site of injury, comprising:
    a plurality of individually-encapsulated single cells, each single cell encapsulated in a dual layer capsule comprising
    (a) an inner layer comprising a therapeutically-effective amount of the cell and a photoinitiator, and
    (b) an outer layer comprising a polymerized hydrogel and substantially surrounding the inner layer, wherein the hydrogel is a gelatin methacrylate (gelMA) and polyethylene glycol diacrylate (PEGDA) hybrid hydrogel.

2. The composition of claim 1, wherein the photoinitiator is anchored to the cell.

3. The composition of claim 1 or 2, wherein the photoinitiator is eosin-isothiocyanate.

4. The composition of claim 1 or 2, wherein the cell is a stem cell.

5. The composition of claim 4, wherein the stem cell is selected from the group consisting of: a mesenchymal linear stem cell (MLC), a hematopoietic stem cell (HSC), and an endothelial progenitor cell (EPC).

6. The composition of claim 1, wherein the cell is selected from the group consisting of jurkat or A549 cells.

7. The composition of claim 1, wherein the photoinitiator is eosin-isothiocyanate and wherein the hydrogel is a gelatin methacrylate (gelMA) and polyethylene glycol diacrylate (PEGDA) hybrid hydrogel, and wherein the cell is selected from the group consisting of: a mesenchymal linear stem cell (MLC), a hematopoietic stem cell (HSC), and an endothelial progenitor cell (EPC).

8. The composition of claim 7, wherein the photoinitiator is anchored to the stem cell.

9. The composition of claim 1, wherein the gelatin methacrylate (gelMA) and polyethylene glycol diacrylate (PEGDA) hybrid hydrogel is formed with about 1 wt % PEGDA added to about 3 wt % gelMA.

10. A method for improving retention of a cell at an in vivo site of injury, comprising: injecting a therapeutically effective amount of the composition of claim 1 to the site of injury.

11. A method for improving retention of a stem cell at an in vivo site of injury, comprising: injecting a therapeutically effective amount of the composition of claim 4 to the site of injury.

12. The method of claim 11, wherein the site of injury is in the myocardium.

13. The method of claim 11, wherein the site of injury is the endothelium.

14. The method of claim 11, wherein the site of injury is an organ.

15. The method of claim 14, wherein the organ is the heart.

* * * * *